US005534017A

United States Patent [19]
van Krieken et al.

[11] Patent Number: 5,534,017
[45] Date of Patent: Jul. 9, 1996

[54] DUAL CHAMBER PACEMAKER SYSTEM WITH IMPROVED RESPONSE TO RETROGRADE CONDUCTION

[75] Inventors: Frits M. van Krieken; Gustaaf A. P. Stoop, both of Dieren, Netherlands

[73] Assignee: Vitatron Medical, B.V., Dieren, Netherlands

[21] Appl. No.: 348,317

[22] Filed: Dec. 2, 1994

[51] Int. Cl.[6] ................................................. A61N 1/362
[52] U.S. Cl. ...................................................... 607/14
[58] Field of Search ..................................... 607/14, 15

[56] References Cited

U.S. PATENT DOCUMENTS

| | | |
|---|---|---|
| 4,401,119 | 8/1983 | Herpers . |
| 4,788,980 | 12/1988 | Mann et al. . |
| 4,890,617 | 1/1990 | Markowitz et al. ...................... 607/14 |
| 4,967,746 | 11/1990 | Vandegriff . |
| 5,247,929 | 9/1993 | Stoop et al. ............................. 607/14 |

Primary Examiner—William E. Kamm
Assistant Examiner—Scott M. Getzow
Attorney, Agent, or Firm—Woodcock Washburn Kurtz Mackiewicz & Norris

[57] ABSTRACT

A dual chamber pacemaker is provided with the capability of determining when there is retrograde conduction, and responding by switching into an asynchronous mode of ventricular pacing. The pacemaker's response to RC further includes delivering at least a first asynchronous ventricular pace pulse at a ventricular escape interval calculated to occur at an appropriate AV delay following the next expected spontaneous natural beat. Thus, the ventricular escape interval can be calculated as $V_{esc}=VA+AA_{avg}+AV_{min}$, where VA is the retrograde time from the prior ventricular pulse to the retrograde atrial sense (or PAC), $AA_{avg}$ is a measure of the average natural atrial rate before retrograde conduction, and $AV_{min}$ is a predetermined value of AV delay. This optimum value of $V_{esc}$ is designed to regain synchronous tracking of the natural sinus after the first extended ventricular pulse. Alternatively, the response can aim to regain tracking in N cycles, where $V_{esc}=AA_{avg}+\Delta$, where $\Delta=(AV_{min}+VA)/N$.

12 Claims, 4 Drawing Sheets

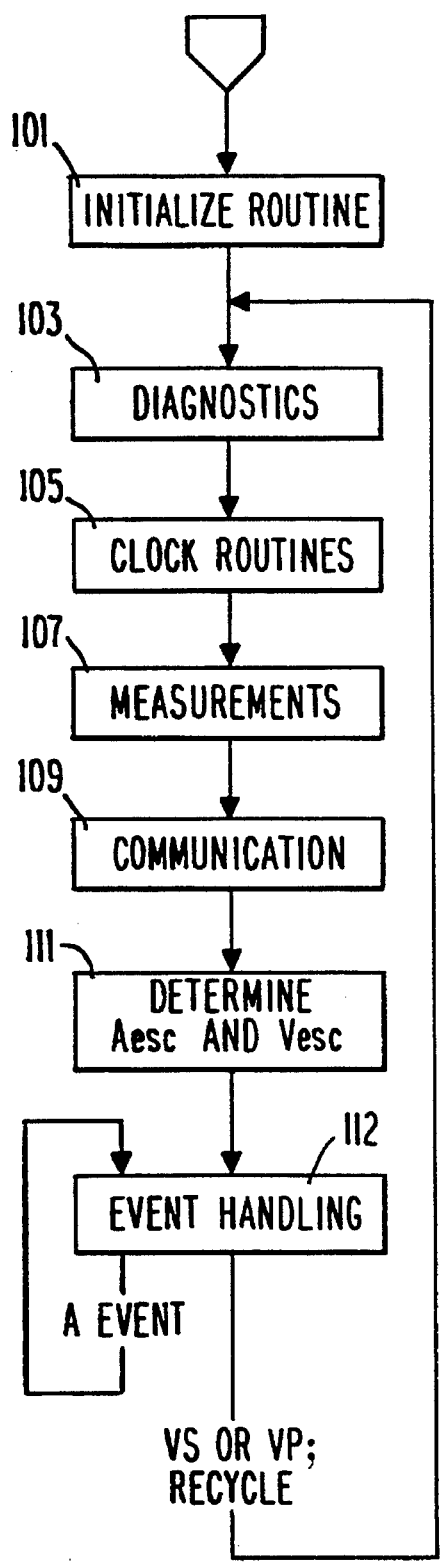
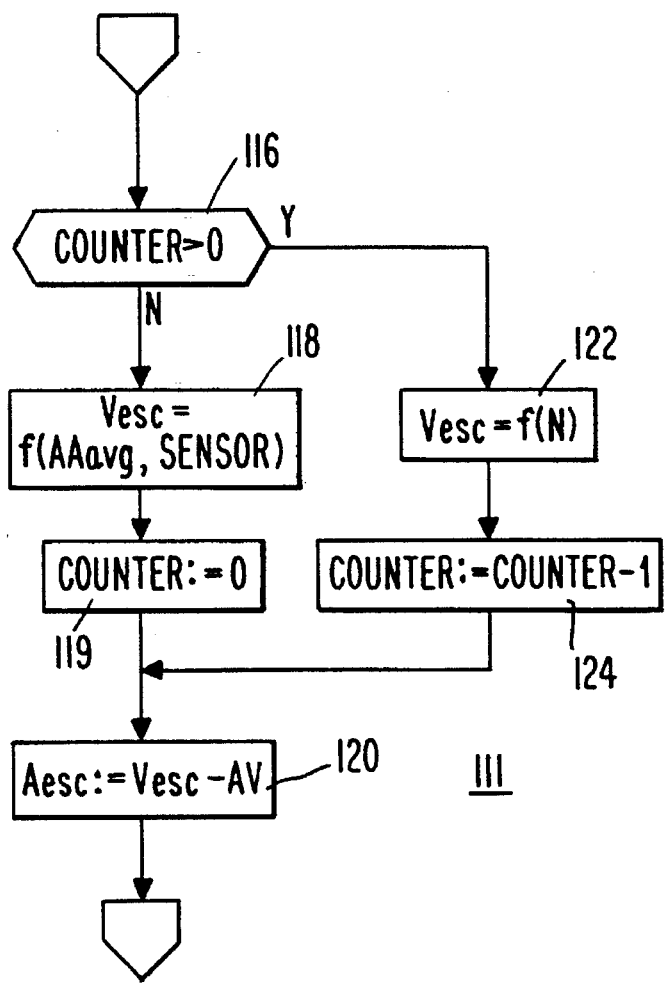
Fig. 3A
Fig. 3B

DUAL CHAMBER PACEMAKER SYSTEM WITH IMPROVED RESPONSE TO RETROGRADE CONDUCTION

FIELD OF THE INVENTION

This invention relates to cardiac pacing systems and, more particularly, to dual chamber pacing systems designed to detect retrograde conduction and to respond actively to return to normal synchronous operation.

DESCRIPTION OF THE PRIOR ART

The advantages of dual chamber pacing, and more particularly pacing in different modes which are selected in response to different patient conditions, is now well recognized in the art. Early pacing systems were solely ventricular, and were sufficient for management of patients with complete heart block and Adams-Stokes attacks. However, ventricular demand pacemakers are not equipped to take advantage of atrial activity, and thus are limited in their efficiency. Subsequently, atrial synchronous, ventricular pacemakers were introduced, having a lead for sensing P signals from the atrium and another for pacing the ventricle after a suitable P-R (A-V) interval. Such a pacemaker, e.g. VDI or VDD, allows the atrium to control the heart's response rate, the ventricle being paced at the atrial rate up to a predetermined upper rate limit. Such synchronous pacers have incorporated means for dealing with high atrial rates, including "block" and "Wenckebach" techniques.

Another form of A-V or dual chamber pacer that has been utilized is the sequential pacemaker (DVI), which paces both the atrium and the ventricle with an appropriate A-V delay which is timed by the pacemaker. A number of commercial pacemakers have been introduced which are programmable to these and other known pacing modes. Each of the various operating modes is particularly adapted to certain circumstances that may arise in a given patient.

Since the dual sense-dual pace DDD pacemaker became commercially available, it has gained favor for the reason that it compensates for many of the disadvantages of other pacemaker modes. The classic DDD pacemaker is described in U.S. Pat. No. 4,920,965, Funke et al., in some detail. See also U.S. Pat. Nos. 4,539,991 and 4,554,921, incorporated herein by reference, which disclose other forms of DDD-type pacemakers.

More recently, the DDDR pacemaker has come to prominence. In this type of pacemaker, there is provided one or more sensors which enable the pacemaker to be rate responsive, such that the pacing interval, or escape interval, is varied as a function of one or more sensed rate-indicating parameters, rather than being fixed at a programmed value. In the DDDR pacemaker, both atrial and ventricular natural beats may occur so long as they occur prior to the respective rate responsive escape interval. See U.S. Pat. Nos. 4,467,807 and 4,951,667, which are illustrative of dual chamber rate responsive pacemakers.

There have also been disclosed multi-mode pacemaker designs having means for switching modes in response to changing patient conditions. Most dual chamber pacemakers are programmable to distinct modes, or switch automatically from one mode to another under certain prescribed conditions. See, for example, U.S. Pat. No. 4,527,568, and U.S. Pat. No. 4,920,965. However, there remains a substantial need in the pacing art for sensing the conditions under which a dual chamber pacemaker can or should be controlled to change mode, and for providing optimum flexibility for blending two or more modes of operation. Thus, instead of forcing the pacer to operate in a distinct mode until patient history enables switching to another distinct mode, the pacer would optimally be enabled to react on a cycle-to-cycle basis to sensed events. For example, while it is desirable to synchronize a delivered ventricular stimulus to a sensed atrial signal whenever possible, at the same time the pacemaker should be controlled to adopt another more optimum response whenever desired. Thus, when a pacemaker detects a condition of retrograde conduction, it is known to switch to a mode of asynchronous ventricular pacing until a natural sinus beat is again detected at a rate which can be tracked. Techniques for detecting retrograde conduction (RC) are known, e.g., U.S. Pat. No. 5,247,929. In such a pacemaker, when RC is detected, there remains the task of breaking the retrograde conduction and returning to synchronous tracking. In a VDD(R) pacemaker, it is necessary to wait for the sinus rhythm to regain control. This normally occurs only when the ventricular rate is sufficiently low. With such sensor rate control, it is possible that a sufficient rate drop will not happen for some time, resulting in pacemaker syndrome. With flywheel control, the rate decrease occurs, but this may take some time, during which again pacemaker syndrome may be manifest. A direct mode switch into asynchronous operation causes immediate lower rate ventricular pacing, but it is a matter of chance when asynchronous pacing is regained. There is thus a need for a pacemaker which responds actively by immediately controlling ventricular pacing at a rate designed to position the pacemaker for a return to synchronous operation.

SUMMARY OF THE INVENTION

It is accordingly an object of the invention to provide a pacemaker that has a means for detecting retrograde conduction, and to further provide for efficient control of ventricular pacing so as to regain synchronous tracking as soon as possible, following detection of RC. When RC is detected, tracking of atrial senses is stopped, e.g. , as in mode switching following start of atrial tachycardia. One or more asynchronous ventricular paces are controlled at a sufficiently low rate, or long escape interval, so as to ensure the resumption of synchronous tracking where a normal atrial sense is available. The longer ventricular escape interval is calculated by obtaining an A—A interval derived recently from the physiological sinus signals, and adding the VA interval (i.e., the retrograde conduction time) and a minimum value for the AV delay ($AV_{min}$). Alternately, the escape interval may be made longer than the A—A interval by a value calculated to restore synchronous tracking after N intervals, assuming that the underlying sinus beats are spontaneously occurring at a constant rate. While applicable to dual chamber pacers generally, the invention is particularly desirable for VDD pacers.

BRIEF DESCRIPTION OF THE DRAWINGS

FIG. 3A is a flow diagram showing the main sequential steps carried out each cycle by the pacemaker of this invention. FIG. 3B is a flow diagram of steps of determining the atrial escape interval ($A_{esc}$) and ventricular escape interval ($V_{esc}$), illustrating an alternate path for determining $V_{esc}$ when RC has been detected.

DESCRIPTION OF THE PREFERRED EMBODIMENTS

Figure 1:
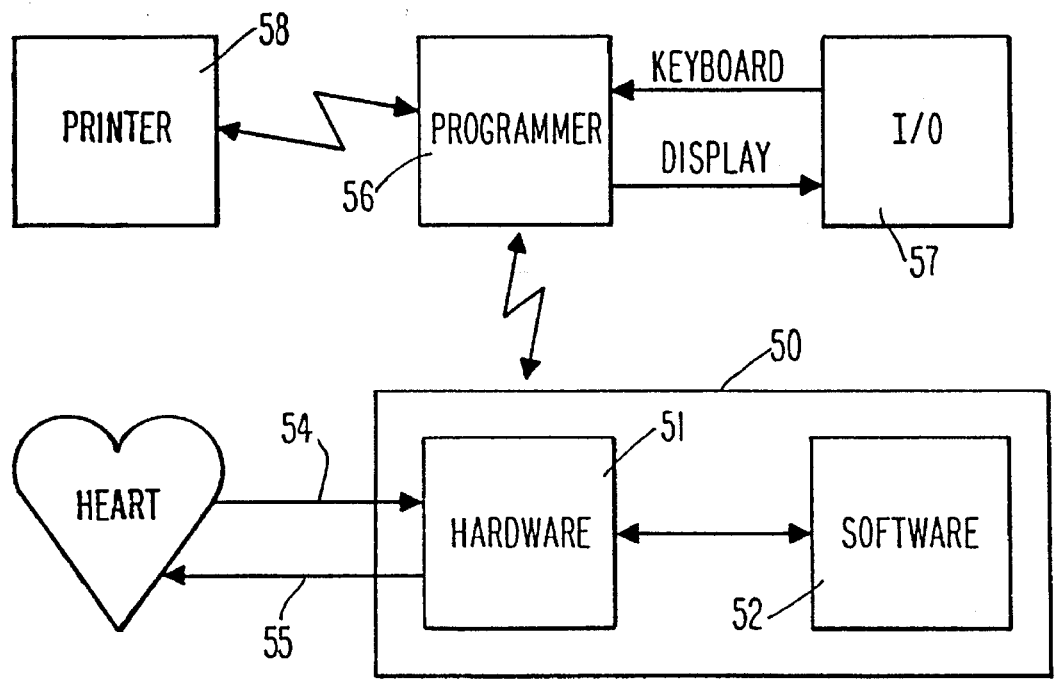
FIG. 1 is a block diagram of the overall system of the invention, showing the environment in which the pacemaker operates.

The pacing system of this invention is preferably software-based, i.e., the software controls functions through hardware, as illustrated in FIG. 1. Referring specifically to FIG. 1, the pacemaker 50 is shown as having a component hardware portion 51 and a software portion 52, the two portions being interconnected. The software is parameter-driven, i.e., there are numerous parameters that control the pacing behavior, diagnostic functions, etc. The hardware is interconnected with the patient's heart by one or more electrodes 55, and one or more sensor connections 54. As is well understood in the art, for a dual chamber pacemaker, there are generally two leads, an atrial lead and a ventricular lead, each lead having at least one electrode, unipole or bipole, positioned in the heart. The line 54 is illustrated as leading to the heart, as in a QT-type sensor arrangement, but may be attached to the outside case of the pacemaker or may couple to any other available sensors for sensing body parameter information used in rate responsive pacing systems. Further, in the preferred embodiment of the pacing system of this invention, sensor link 54 may comprise a pair of sensors, e.g., QT plus activity, as set forth in U.S. Pat. No. 5,065,759.

As further illustrated in FIG. 1, the pacer 50 is in telemetric communication with a programmer 56. The user can select parameters and program them through programmer 56, and can also interrogate parameter and diagnostic data from the implanted pacemaker. Interrogated information from the pacer can be coupled by telemetry directly to a printer 58. Input/output devices 57 are used to input information by the user to the programmer, or to display information received by the programmer from the pacemaker.

Figure 2:
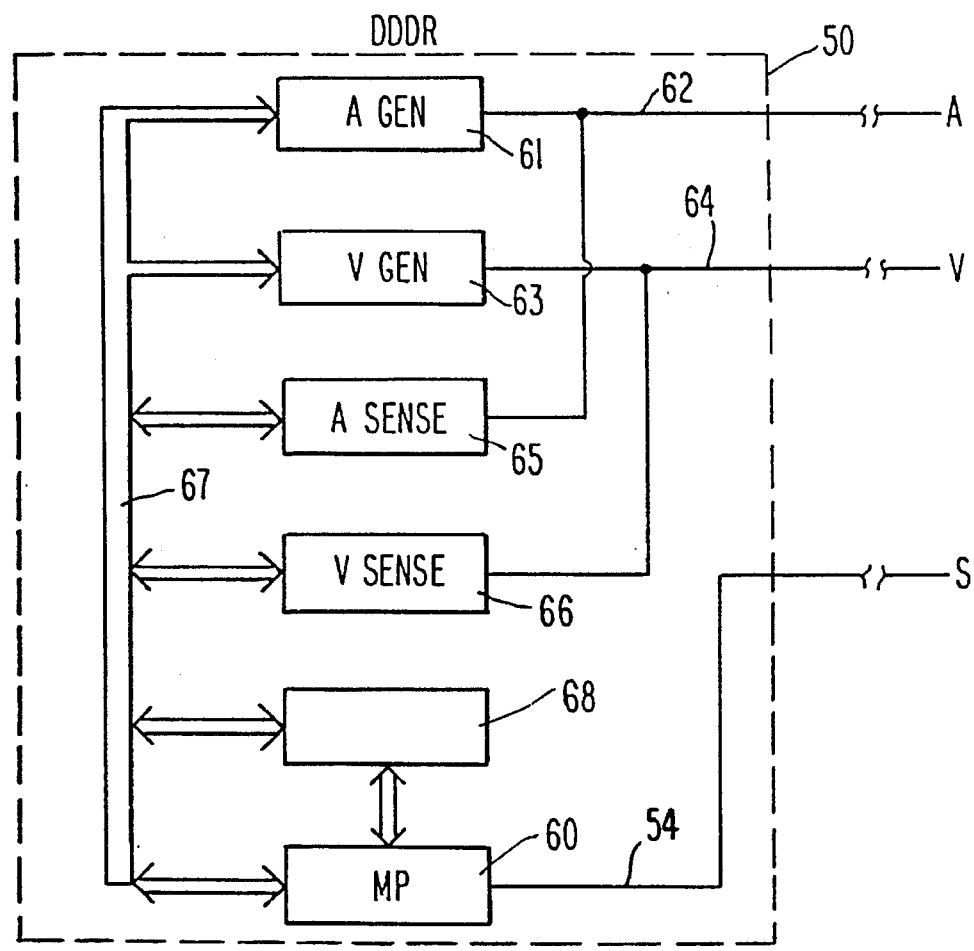
FIG. 2 is a block diagram which illustrates basic components of the pacemaker of this invention, together with leads and a sensor for delivering signals to and/or receiving signals from the patient.

Referring to FIG. 2, there is shown a basic block diagram of primary hardware components of a DDDR pacer 50. An atrial generator 61 is shown, having an output connected to lead 62 which communicates with the patient's atrium. An A-sense amplifier 65 is illustrated also connected to atrial lead 62. A ventricular generator is illustrated which is connected to the patient's ventricle through lead 64. V-sense amplifier 66 is also connected to lead 64, to receive and sense signals from the patient's ventricle. In one embodiment of this invention which preferably incorporates QT rate control, V-sense block 66 also includes means for picking out and determining the timing of the evoked T wave. Generators 61 and 63 and sense blocks 65 and 66 are interconnected with microprocessor system 60, which microprocessor has software which is parameter-driven to control the operation of the hardware units. Microprocessor system 60 may be interconnected with hardware logic and/or timing circuits 68. As affects the scope of this invention, the degree to which software supplants hardware, or vice versa, is a matter of design choice. Thus, for the many timing functions that are carried out in the pacing system of this invention, it is to be understood that the microprocessor may have built in timing circuits, or suitably may control external hardware timer circuits. Software control of pacing function is well known in the art, such that the following detailed discussions of software routines enable one of ordinary skill in this art area to design a system for carrying out the functions within the scope of the invention. Data inputted from programmer 56 is stored in memory associated with microprocessor.

Still referring to FIG. 2, there is shown a sensor S indicated as providing an input to microprocessor system 60. Sensor S represents one or more sensors for monitoring one or more body parameters to provide an indication of desired pacing rate. The pacemaker of this invention may be rate responsive in the manner as described in the referenced U.S. Pat. No. 5,247,930.

Referring now to FIG. 3A, there is shown a flow diagram of the main routines taken each cycle by the pacemaker of this invention. The routine is initialized at 101. Following this, any diagnostics built into the pacer are performed at block 103; clock routines are done at block 105; measurements are performed and measure data stored at 107; and any communications with an external device, such as programmer 56, are done at step 109. The routine then goes to step 111, and determines $A_{esc}$ and Vest for the coming cycle. Of course, for a VDD pacer, no $A_{esc}$ is determined. Following this, the pacemaker carries out event handling at 112, i.e., it reacts to atrial and/or ventricular senses, and delivers pace pulses as required by timeout of escape intervals. Following the ventricular event, either VS or VP, the pacer returns for the next cycle.

Referring now to FIG. 3B, these are illustrated the primary steps for determining $A_{esc}$ and $V_{esc}$, i.e., block 111 of FIG. 3A. At 116, it is determined whether RC has been detected. In this embodiment the pacemaker checks to see if an RC counter has a value greater than 0. The role of the counter is explained further in connection with the discussion of FIGS. 4B and 5; at this point block 116 can simply be understood as the step of checking to see if RC has been detected. If not, the pacemaker goes to step 118, and sets $V_{esc}$ in a conventional manner. Thus, as indicated, $V_{esc}$ can be set as a function of the sinus rate, i.e., track the patient's natural rate if available, or can be rate responsive to sensor data. Following this, $A_{esc}$ is set equal to $V_{esc}$–AV, where AV can be a programmed value or otherwise determined by the pacer. Alternately, if it is determined at 116 that there is RC, the pacer goes to step 122 and determines $V_{esc}$ in accordance with this invention, where $V_{esc}$=f(N). As explained below, $V_{esc}$=f(N) is calculated for optimal return to tracking of the patient's existing natural sinus beat. At step 124 the counter is decremented by 1, such that the special determination of $V_{esc}$=f(N) is carried out for at most N ventricular pace pulses.

Figure 4A:
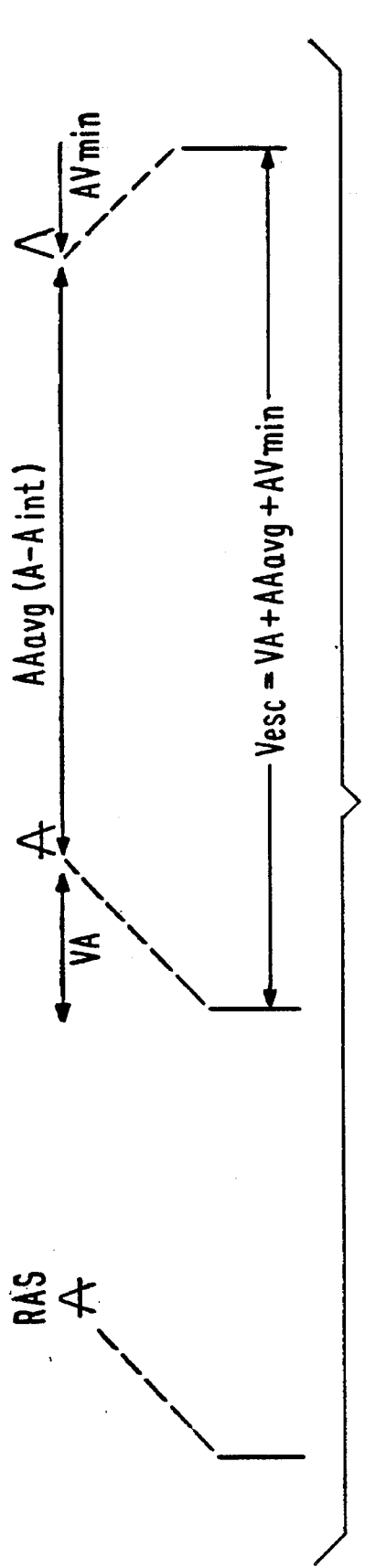
FIG. 4A is a timing diagram which illustrates the optimum ventricular escape interval for regaining synchronous tracking after a retrograde atrial sense.

Referring now to FIG. 4A, there is shown a timing diagram illustrating the derivation of optimum of $V_{esc}$ for achieving resync at the next expected sinus sense following a retrograde atrial sense (RAS). As illustrated, a ventricular pace results in retrograde conduction and an RAS. This combination of VP followed by RAS is shown again, the time between the VP and RAS being indicated as VA. The timing diagram illustrates the time between the second RAS and the next expected spontaneous sinus beat. This time is expressed as $AA_{Avg}$, which is obtained by the pacemaker by keeping a running average of the sinus rate, or alternately from the rate response sensor information. As can be seen from the timing diagram, in order to resync at the next expected natural sinus sense (AS), the calculated escape interval should be of a duration so as to extend beyond the next expected AS by the minimum AV delay, or $AV_{min}$. Thus, the calculated shortest value of $V_{esc}$ for delivery of the next VP so as to allow proper sync of the expected sinus beat is $VA+AA_{Avg}+AV_{min}$. Accordingly, when retrograde conduction has been determined by the pacemaker, the following formula applies for calculating the ventricular escape interval in order to achieve resync following the next atrial sense:

$$V_{esc}=VA+AA_{Avg}+AV_{min}$$

Figure 4B:
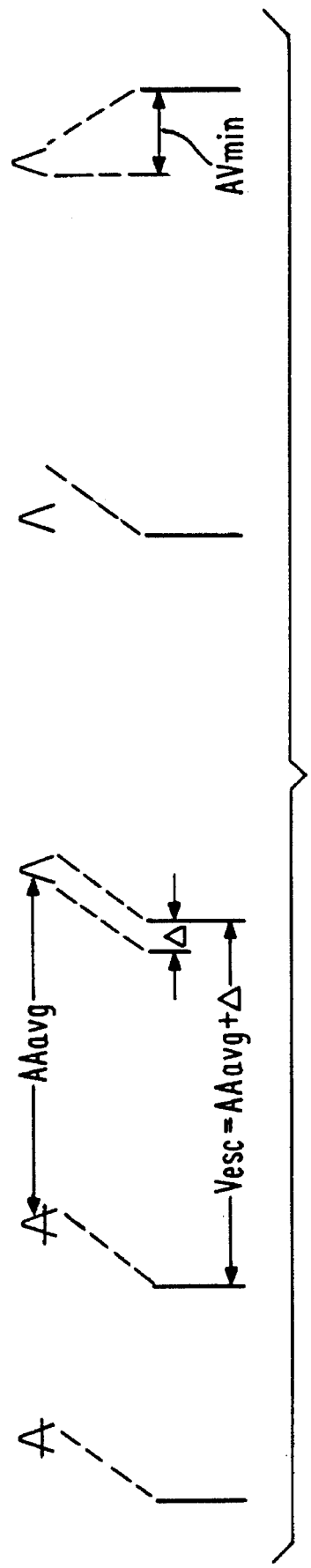
FIG. 4B is a timing diagram illustrating the operation of the pacemaker of this invention wherein delivery three ventricular pace pulses are delivered with an extended $V_{esc}$ designed to regain synchronous tracking of the natural atrial beats.

It is recognized that the above formula for $V_{esc}$ results in a long V—V interval. Assuming that it is desired to avoid such a long interval, and gradually achieve resynchronization in a short number of cycles (N), then the technique of FIG. 4B can be used. Here, the escape interval is set equal to the $AA_{Avg}$ interval plus a factor $\Delta$, where $\Delta=(AV_{min}+VA)/N$. This formula recognizes that the ventricular pace pulses are to be delayed by $AV_{min}+VA$ relative to the natural sinus beats, and this delay is to occur over N cycles. Thus, if the pacemaker delays successive VPs so as to achieve resync after N cycles, $\Delta$ must be set to $(AV_{min}+VA)/N$. In the illustration of FIG. 4B, N=3, and the third VP is delivered $AV_{min}$ after the third spontaneous AS. Note that the first VP with an extended $V_{esc}$ in this illustration does not cause an RAS, because the retrograde conduction path finds the atrium refractory due to the sinus beat. Likewise the next VP occurs at about the time of the expected sinus beat and also finds the atrium still refractory. Synchronization is achieved with the third cycle of the sequence. Note that if N=1, then the first ventricular pace pulse is delivered with an escape interval, $V_{esc}=VA+AA_{avg}+Av_{min}$.

Figure 5:
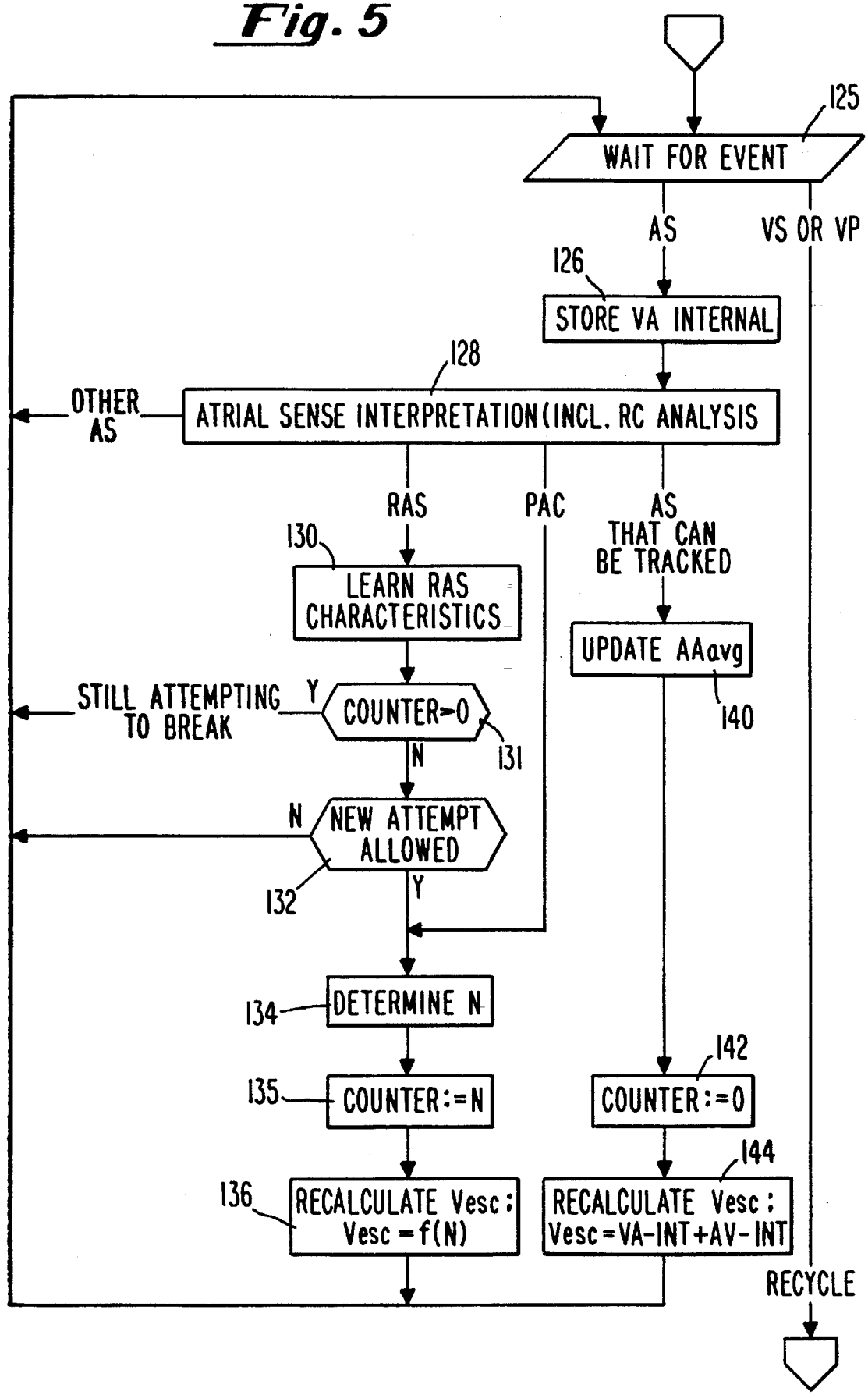
FIG. 5 is a flow diagram showing the primary steps taken by the pacemaker of this invention in responding to detection of RC by delivery one or more asynchronous ventricular pace pulses at a $V_{esc}$ calculated in accordance with this invention.

Referring now to FIG. 5, there is shown a flow diagram which represents the specific steps taken in order to respond to retrograde conduction in accordance with this invention. It is to be understood that this flow diagram does not include all steps taken by the pacemaker each cycle, but shows the organization for adapting the ventricular escape interval so as to achieve quick resynchronization after RC. FIG. 5 assumes a VDD pacemaker, and thus makes no provision for an atrial pulse.

At 125 the pacemaker is waiting for a next event, either atrial or ventricular. If there is an AS, at block 126 the pacemaker determines and stores the VA interval. Then at block 128 the pacemaker goes through atrial sense interpretation, i.e., it examines the relative timing of the atrial sense and categorizes it for logic purposes. The pacer also does an RC analysis. The analysis for determining RC in the first instance may be any available technique, and as such is not specific to this invention. See, for example, U.S. Pat. No. 5,247,929, incorporated herein by reference, which discloses a pacemaker with means for determining RC, as well as atrial sense interpretation generally.

If an RAS is identified, the pacemaker goes to block 130 and stores information concerning the characteristics of the RAS in order to learn the patient's RAS characteristics and update the RC analysis. Then, at 131, it is determined whether RC just started, i.e., is the counter at 0. If the counter is greater than 0, the pacer is still attempting to break RC, and exits this routine. If the counter is at 0, the pacer goes to step 132 to see if a new attempt at ending RC is allowed. At this point, the pacer determines whether the last previous attempt to break RC was long ago, e.g., some predetermined number of cycles such as 64 or 128. If the answer is no, the pacemaker wants to wait longer before trying again, and branches back to block 125. If yes, the routine goes to block 134 and determines N, i.e., the number of cycles within which it is aimed to achieve resynchronization. It is preferable for the pacemaker to determine an optimal value for N, such that it is not greater than a maximum programmed value, and such that the resulting lengthened $V_{esc}$ remains less than a programmed length, either expressed in ms or as a percentage (>100%) of the previous $V_{esc}$ or $A-A_{avg}$. Alternately, N may simply be programmed into the pacer. In most applications, N will be within the range 1–3. At block 135, the counter is set to the determined value of N. Then the $V_{esc}$ (N) is determined at 136, being the lengthened $V_{esc}$ for achieving resync, according to the above formula.

Returning to block 128, if an RAS has not been identified, but there is a PAC resembling RAS, then it is treated as an RAS and the program branches to block 134. If the atrial sense interpretation reveals an AS that can be tracked, the routine goes to block 140 and updates $AA_{avg}$. It then goes to block 142 and resets the counter to 0. Then, at block 144, the pacer sets $V_{esc}$ to the normal value of VA-int+AV-int. And lastly, if at block 128 there is no interpretation of an RAS, PAC or AS that can be tracked, the AS is interpreted as "other AS", and the routine returns to 125 and waits. This happens when and if there is a detected AS after RC is detected, as illustrated in FIG. 4B.

Returning to block 125, when the event is a V event, the pacemaker has either sensed a VS, or delivered a VP. The routine then exits.

There is thus provided a dual chamber pacer, particularly in a VDD embodiment, with an improved capacity for reacting to a detected RC condition. The pacer determines a $V_{esc}$ for one or more asynchronous pacer pulses, where $V_{esc}$ is calculated to optimally return the pacer to synchronous tracking of the patient's sinus beats.

What is claimed is:

1. A dual chamber pacemaker having atrial sense means for sensing signals from a patient's atrium, sinus interval means for determining an interval (A—A Int) representative of the patient's underlying sinus rate, ventricular pace means for generating pace pulses for delivery to the patient's ventricle, control means for controlling the timing of said pace pulses, and interpretation means for interpreting when a said atrial sense can be tracked and when a said atrial sense indicates RC, said control means further comprising tracking means for controlling said pace means to generate pace pulses in tracking relation to sensed atrial signals when said interpreting means interprets that they can be tracked, and asynchronous means for controlling said pace means to deliver at least one asynchronous pulse following an atrial sense interpreted as indicating RC, said asynchronous means further having timing means for controlling said pace means to deliver said at least one pulse at a time more than said sinus interval following said indicating atrial sense.

2. The pacemaker as described in claim 1, wherein said timing means controls delivery of said at least one pulse at an escape interval $V_{esc}=VA+A—A\ Int+AV_{min}$, where VA is the time from the prior ventricular pulse to the indicating sense, and $AV_{min}$ is a predetermined minimum value of AV delay.

3. The pacemaker as described in claim 1, wherein said timing means controls delivery of N pulses each having an escape interval $V_{esc}=A—A\ Int+\Delta$, where $\Delta=(AV_{min}+VA)/N$, where VA is the time from the prior ventricular pulse to the indicating sense, and $AV_{min}$ is a predetermined minimum value of AV delay.

4. A dual chamber pacemaker having atrial sense means for sensing signals from a patient's atrium, sinus means for determining a sinus interval corresponding to the patient's spontaneous underlying sinus rhythm, ventricular pace means for generating pace pulses for delivery to a patient's ventricle, control means for setting the V—V interval of said ventricular pace pulses, VA means for measuring the VA interval between a ventricular pace and an atrial sense, and AS interpretation means for identifying atrial senses having the potential to have resulted from retrograde conduction, said control means having RC means responsive to a said identified atrial sense for controlling said ventricular pace means to deliver at least a next ventricular pace pulse at a V—V interval greater than the last VA interval, plus said sinus interval.

5. The pacemaker as described in claim 4, wherein said RC means is operative for controlling said ventricular pace means to deliver a plurality of pace pulses, each of said plurality of pace pulses being at a V—V interval greater said last VA interval plus said sinus interval.

6. The pacemaker as described in claim 4, comprising limit means for limiting said RC means to be operative for no more than N consecutive cycles.

7. A dual chamber pacemaker having atrial sense means for sensing signals from a patient's atrium, ventricular pace means for delivering pace pulses to a patient's ventricle, means for obtaining an A—A interval which is a measure of the patient's atrial rate, control means for controlling said ventricular pace means to deliver ventricular pace pulses at the time out of a ventricular escape interval, RC detect means for detecting a state of retrograde conduction (RC), and response means for responding to said RC state, said response means comprising $V_{esc}$ means for setting an extended ventricular escape interval to time out at a calculated duration after the last sensed atrial signal, said duration being greater than said A—A interval.

8. The pacemaker as described in claim 7 wherein said $V_{esc}$ means sets said duration equal to said A—A interval plus $AV_{min}$, wherein $AV_{min}$ represents a predetermined minimum value of said AV delay.

9. The pacemaker as described in claim 7, wherein said response means has async means for controlling said pace means to pace asynchronously at said extended escape interval until said RC state terminates or for N cycles, whichever occurs first.

10. The pacemaker as described in claim 9, wherein N equals 3.

11. The pacemaker as described in claim 7, wherein said control means has sync means for sensing when a sensed atrial signal can be tracked and for setting said ventricular escape interval to time out at a predetermined AV delay following a sensed atrial signal that can be tracked.

12. The pacemaker as described in claim 7, wherein said dual chamber pacemaker is a VDD pacemaker.

* * * * *